United States Patent
Wiig et al.

(10) Patent No.: US 8,563,806 B2
(45) Date of Patent: Oct. 22, 2013

(54) NEMATODE INDUCIBLE PROMOTORS AND METHODS OF USE

(75) Inventors: Aaron Wiig, Chapel Hill, NC (US); Robert Ascenzi, Cary, NC (US); Xiang Huang, Apex, NC (US); Sumita Chaudhuri, Cary, NC (US); Rui-Guang Zhen, Chapel Hill, NC (US); Yu Han, Cary, NC (US)

(73) Assignee: BASF Plant Science GmbH (DE)

( * ) Notice: Subject to any disclaimer, the term of this patent is extended or adjusted under 35 U.S.C. 154(b) by 771 days.

(21) Appl. No.: 12/522,260

(22) PCT Filed: Feb. 4, 2008

(86) PCT No.: PCT/EP2008/051329
§ 371 (c)(1),
(2), (4) Date: Jul. 7, 2009

(87) PCT Pub. No.: WO2008/095888
PCT Pub. Date: Aug. 14, 2008

(65) Prior Publication Data
US 2010/0043102 A1    Feb. 18, 2010

Related U.S. Application Data

(60) Provisional application No. 60/899,693, filed on Feb. 6, 2007.

(51) Int. Cl.
*C12N 15/82* (2006.01)
*C12N 15/87* (2006.01)
*C12N 15/63* (2006.01)

(52) U.S. Cl.
USPC .................. 800/287; 536/24.1; 435/320.1

(58) Field of Classification Search
USPC ......................................................... 800/287
See application file for complete search history.

(56) References Cited

U.S. PATENT DOCUMENTS 7,439,348 B2 * 10/2008 Diehn et al. ................. 536/24.1

FOREIGN PATENT DOCUMENTS

WO   WO 2006/102343 A2   9/2006
WO   WO 2006/102343 A3   9/2006

OTHER PUBLICATIONS

Nakamura et al. 2004, Genbank accession: AB007727.*
Database EMBL "*Arabidopsis thaliana* genomic DNA chromosome 5, Pl clone: MXC9." XP002477228 EBI accession No. EMBL:AB007727 see nucleotides 40530 to 42005, 2004.

* cited by examiner

*Primary Examiner* — Li Zheng
(74) *Attorney, Agent, or Firm* — Patricia A. McDaniels

(57) ABSTRACT

The invention provides isolated promoter polynucleotides that are root-specific and/or induced by plant parasitic nematodes. The promoters of the invention are useful for controlling expression of nucleic acids of interest in plant roots and are particularly useful for controlling transcription of nucleic acids encoding agents that disrupt formation or maintenance of parasitic nematode feeding sites in plants.

9 Claims, 9 Drawing Sheets

Figure 1

```
   1    GCTCGCGTTA GTTCCACTCA AGGAGTATCC TTTCTTCCTT GCGCAACTCT
  51    CCACCTTCGG GTAAAGTACC ATCTCTAGCA TCTTGAGTCT TGATCAACTT
 101    CTGTTTTGCT TACTCTCAAA ATGCATTAAT TTTTTTTAT ACTAGATCAT
 151    AGTATTATAT CTCTTAATCT ACCTATTGAA ATCTACTTAA TGTTTTTACT
 201    AAAACCTACG TGTTTCTCTT TAGAGAATTT TGTGCTATGC ATGAATTAGA
 251    GGTTAGTAAT GTGTAATACT TCATAAGTCT AGATTTATTT GTTGGTTAAC
 301    ACGTTTAGTA ATTCACACAC ACACACCACC TTAGATATTT TACTGTGAAT
 351    TAGAAAAAGA TACATAGTTA GGAGTGTTTT TTTAAAAAAA TTCAATCATG
 401    AGAAAATTAG AGGTGTGATG TTATACATTA TGAAAATGCA AAGGGCAGAT
 451    ACGAATAAAT TAGAAACTTG TTTAACGGGT CAGAGTTGGC TTCTAGTCTC
 501    TTTCGACTTG GATACTTCTT CTTCTACAAT TGGGACATTA TTGTAGGCGC
 551    ATTATATCAT TTCTCTACAT GCAATGAATG TACATACATT AATTCACATT
 601    TATTTTTGGA ATAATCATAT GAGTGATCGA AGTTTGTATT TATATATTCA
 651    ATCTTCACAA ACTACTTTTA TTTAAAAATC ATTTGCAAAA TGCTATTTTA
 701    TTGACAAAAA GATATATGCT ATAAAATAAA ATAAAATTCA CAAACTATAG
 751    TCATTAATAC AAAAAGAAAT CATTGAATAT GGTAGAGGGG AAACAAAAAA
 801    AAAACACGAC GATGTAAGTT GGTGGAACCA CATTATCAAA ATAAAAGAAG
 851    GTGGTGGAAC CAAATTGAAT AAAGTCCGTC CATATCATTA TCCGTCCCTT
 901    AGGAGCCTCT AATTAGTAAT ATTCTTATGG GTCCACTGTG GCTTAGAGGA
 951    CTTGATTAAA ACCATTCTTA TTTAGTGCTA ACTTTGTGAG GGTTGGAATA
1001    ACGAACCAAG CTGATTCAAA CCATTCCAAA ACAAAGTTGT CACATATTTC
1051    AAAACCAAAG TTTACCGGAC AGAGAAATAT GGTGTGTTTT TCTCAAACCA
1101    AGCTAAATGG AATCCATTGT AAACCAAAAT GTTCACACCT ACCTATTCTT
1151    TTGGAGTCCC TTTTCCATGT GTTTGCTGTC TGCTAGTCAA GTTCATTAG
1201    CTGATTGCCT TGCATCATAT TCTTGGATCA ACTTTTTTTT TTTTTTTTT
1251    TGGGGTAATT AACAAAATGC TTAAATTTCT CAAGACTATA GGATCACATT
1301    ACCTGTGTGC TTAACATAAC TTTTAGATAG GCTAGAGAAT TGATCTATTA
1351    CAAGATAATC AATAATTTAC AGAAGAAAAC ATTCTTTTTT TTGTTCTATT
1401    TCCTTCATGT AGGTATGTAG CTGTATATTA TACTATCTTG TATTTTCGAT
1451    ATCGTGCTGG AACTGTCACA GATGCA   (SEQ ID NO:1)
```

Figure 2

```
  1  AAGATGGTGC AGCCTGCTTC CTAAATTTTG GTACATTATC AAGTGGATGT
 51  GATGGTGCCC CTCTGCTTCC TCTGCTGTTT ATTATTGTAA ACATAGGTTT
101  CAATATTGCA TTGCTTCATC TCCTCAAGAT CTCTTCAGCT GTTGTATCTT
151  GTCTTGCTTC CACATTTTCA GTCCCAATAT CCATCTACGT GTTCACCATG
201  CCATTGCCAT ACCTTGGTGT TGCCTCCTCT CTTCCAACAG GCTTTATGGC
251  AGGGGCCATT ATCCTCATTT TGGGCTTACT CATTTATGCT TGGACCCCTT
301  CAAATGGTTC CTCGGGTGCT TCCTTCTCAA CTTCCTCCAC CTAGAGAGGC
351  TAGAATGAGT TGACATGTCA TTGCAGATAG TACAACACCA CAAGGAACTA
401  ATTCAGGTTC GCTTTTAGGA GACGGCTATA AGAAGGAGAA AGAAATAGGG
451  CGTTCTTGTA AGTTGTAATA GTTGTTCGTA AGCATTTTTT ATGAGCTAAG
501  CTTAAGTAAG AAAGAGACTA GACTATAGAT AGAACAGGTT CCAAGTTCAA
551  TTTTTATGTA AGCTAAGGAA AGTAAATAGA GAATAAAAGT CACTTTGTTG
601  ACAGAGGAAA TGATATTGGA CCATTTGGAT GCAAAAAAAA AAAAAAA
     (SEQ ID NO:2)
```

Figure 3

```
  1  DGAACFLNFG  TLSSGCDGAP  LLPLLFIIVN  IGFNIALLHL  LKISSAVVSC
 51  LASTFSVPIS  IYVFTMPLPY  LGVASSLPTG  FMAGAIILIL  GLLIYAWTPS
101  NGSSGASFST  SST*    (SEQ ID NO:3)
```

Figure 4

| Gene Name | Syncytia #1(N)¶ | Syncytia #2 (N) | Non-Syncytia | Untreated Root |
|---|---|---|---|---|
| 50657480§ | 299±47 (4) | 369±57 (5) | ND* | ND |

Figure 5

```
  1  MLSVPKSPFL IVGILEALAA AAGMAAAANL SGPSTTVLSQ RKPNTRMYSC
 51  SSRCNRQCGK VRSAFVLIFC GSGAAHSLNE AGVLWILLMV LSFLLQGAGT
101  VLKEVIFIDS QRRLKGASLD LFIVNSYGSA FQAICIALLL PFLSKLWGIP
151  FNQLGTYLKD GAVCFLNNGT ITKGCDGAPF LPLLFVIMNI GYNIALLRLL
201  KISSAVVSCL ASTVSVPIAV FLFTMPLPYL GVASSLPKGF MGGTIILVLG
251  MILYSWTPHG ANSSHTDSVI PSPPPT*   (SEQ ID NO:4)
```

Figure 6

```
                    1                                                50
SEQ ID NO:3   (1)   --------------------------------------------------
SEQ ID NO:4   (1)   MLSVPKSPFLIVGILEALAAAAGMAAAANLSGPSTTVLSQRKPNTRMYSC 51                                               100
SEQ ID NO:3   (1)   --------------------------------------------------
SEQ ID NO:4  (51)   SSRCNRQCGKVRSAFVLIFCGSGAAHSLNEAGVLWILLMVLSFLLQGAGT 101                                              150
SEQ ID NO:3   (1)   --------------------------------------------------
SEQ ID NO:4 (101)   VLKEVIFIDSQRRLKGASLDLFIVNSYGSAFQAICIALLLPFLSKLWGIP 151                                              200
SEQ ID NO:3   (1)   ---------DGAACFLNFGTLSSGCDGAPLLPLLFIIVNIGFNIALLHLL
SEQ ID NO:4 (151)   FNQLGTYLKDGAVCFLNNGTITKGCDGAPFLPLLFVIMNIGYNIALLRLL 201                                              250
SEQ ID NO:3  (42)   KISSAVVSCLASTFSVPISIYVFTMPLPYLGVASSLPTGFMAGAIILILG
SEQ ID NO:4 (201)   KISSAVVSCLASTVSVPIAVFLFTMPLPYLGVASSLPKGFMGGTIILVLG 251              277
SEQ ID NO:3  (92)   LLIYAWTPSNGSSGASFSTSST-----
SEQ ID NO:4 (251)   MILYSWTPHGANSSHTDSVIPSPPPT-
```

Figure 7

Nematode infected:

| SeqID | Construct | Root tip | Vascular | Cortical | Syncytia |
|---|---|---|---|---|---|
| 1 | pAW280 | - | -/+ | - | ++ |

Control uninfected:

| SeqID | Construct | Root tip | Vascular | Cortical |
|---|---|---|---|---|
| 1 | pAW280 | - | -/+ | - |

Figure 8

Nematode infected:

| SeqID | Construct | Root tip | Vascular | Cortical | Syncytia |
|---|---|---|---|---|---|
| 1 | pAW280 | - | -/+ | - | ++ |
|  | RTJ119 | - | -/+ | - | + |
|  | RTJ120 | - | - | - | - |

Control uninfected:

| SeqID | Construct | Root tip | Vascular | Cortical |
|---|---|---|---|---|
| 1 | pAW280 | - | -/+ | - |
| 1 | RTJ119 | - | -/+ | - |
|  | RTJ120 | - | -/+ | - |

Figure 9

| Common Primer | SEQ ID NO | Sequence 5' to 3' |
| --- | --- | --- |
| At5g12170For | 5 | CCCGGGGCTCGCGTTAGTTCCACTC |
| At5g12170Rev | 6 | GGCGCGCCTGCATCTGTGACAGTTCCAG |
| pAW280pr1kbFor | 7 | ACGTCTGCAGCGGGTCAGAGTTGGCTTC |
| pAW280pr500bpFor | 8 | AGCTCTGCAGGCTAACTTTGTGAGGGTTG |
| pAW280prRev | 9 | TGCAGGCGCGCCTGCATCTGTG |

NEMATODE INDUCIBLE PROMOTORS AND METHODS OF USE

CROSS-REFERENCE TO RELATED APPLICATIONS

This application is a national stage application under 35 U.S.C. §371 of PCT/EP2008/051329, filed Feb. 4, 2008, which claims benefit of U.S. provisional application No. 60/899,693, filed Feb. 6, 2007. The entire contents of each of the above-identified applications are incorporated herein by reference.

FIELD OF THE INVENTION

This invention relates to the promoter and fragments thereof that regulate transcription of the *Arabidopsis thaliana* identifier At5g12170. The promoters of the invention are useful for controlling transcription of any nucleic acid of interest in plant roots. In particular, the promoters of the invention may be used to control transcription of nucleic acids encoding agents that disrupt the formation or maintenance of the feeding site, disrupt the growth and/or reproduction of plant parasitic nematodes, that confer or improve plant resistance to plant parasitic nematodes, or that are toxic to plant parasitic nematodes to reduce crop destruction.

BACKGROUND OF THE INVENTION

Nematodes are microscopic roundworms that feed on the roots, leaves and stems of more than 2,000 row crops, vegetables, fruits, and ornamental plants, causing an estimated $100 billion crop loss worldwide. A variety of parasitic nematode species infect crop plants, including root-knot nematodes (RKN), cyst- and lesion-forming nematodes. Root-knot nematodes, which are characterized by causing root gall formation at feeding sites, have a relatively broad host range and are therefore pathogenic on a large number of crop species. The cyst- and lesion-forming nematode species have a more limited host range, but still cause considerable losses in susceptible crops.

Pathogenic nematodes are present throughout the United States, with the greatest concentrations occurring in the warm, humid regions of the South and West and in sandy soils. Soybean cyst nematode (*Heterodera glycines*), the most serious pest of soybean plants, was first discovered in the United States in North Carolina in 1954. Some areas are so heavily infested by soybean cyst nematode (SCN) that soybean production is no longer economically possible without control measures. Although soybean is the major economic crop attacked by SCN, SCN parasitizes some fifty hosts in total, including field crops, vegetables, ornamentals, and weeds.

Signs of nematode damage include stunting and yellowing of leaves, and wilting of the plants during hot periods. However, nematode infestation can cause significant yield losses without any obvious above-ground disease symptoms. The primary causes of yield reduction are due to root damage underground. Roots infected by SCN are dwarfed or stunted. Nematode infestation also can decrease the number of nitrogen-fixing nodules on the roots, and may make the roots more susceptible to attacks by other soil-borne plant pathogens.

The nematode life cycle has three major stages: egg, juvenile, and adult. The life cycle varies between species of nematodes. For example, the SCN life cycle can usually be completed in 24 to 30 days under optimum conditions whereas other species can take as long as a year, or longer, to complete the life cycle. When temperature and moisture levels become favorable in the spring, worm-shaped juveniles hatch from eggs in the soil. Only nematodes in the juvenile developmental stage are capable of infecting soybean roots.

The life cycle of SCN has been the subject of many studies, and as such are a useful example for understanding the nematode life cycle. After penetrating soybean roots, SCN juveniles move through the root until they contact vascular tissue, at which time they stop migrating and begin to feed. With a stylet, the nematode injects secretions that modify certain root cells and transform them into specialized feeding sites. The root cells are morphologically transformed into large multinucleate syncytia (or giant cells in the case of RKN), which are used as a source of nutrients for the nematodes. The actively feeding nematodes thus steal essential nutrients from the plant resulting in yield loss. As female nematodes feed, they swell and eventually become so large that their bodies break through the root tissue and are exposed on the surface of the root.

After a period of feeding, male SCN nematodes, which are not swollen as adults, migrate out of the root into the soil and fertilize the enlarged adult females. The males then die, while the females remain attached to the root system and continue to feed. The eggs in the swollen females begin developing, initially in a mass or egg sac outside the body, and then later within the nematode body cavity. Eventually the entire adult female body cavity is filled with eggs, and the nematode dies. It is the egg-filled body of the dead female that is referred to as the cyst. Cysts eventually dislodge and are found free in the soil. The walls of the cyst become very tough, providing excellent protection for the approximately 200 to 400 eggs contained within. SCN eggs survive within the cyst until proper hatching conditions occur. Although many of the eggs may hatch within the first year, many also will survive within the protective cysts for several years.

A nematode can move through the soil only a few inches per year on its own power. However, nematode infestation can be spread substantial distances in a variety of ways. Anything that can move infested soil is capable of spreading the infestation, including farm machinery, vehicles and tools, wind, water, animals, and farm workers. Seed sized particles of soil often contaminate harvested seed. Consequently, nematode infestation can be spread when contaminated seed from infested fields is planted in non-infested fields. There is even evidence that certain nematode species can be spread by birds. Only some of these causes can be prevented.

Traditional practices for managing nematode infestation include: maintaining proper soil nutrients and soil pH levels in nematode-infested land; controlling other plant diseases, as well as insect and weed pests; using sanitation practices such as plowing, planting, and cultivating of nematode-infested fields only after working non-infested fields; cleaning equipment thoroughly with high pressure water or steam after working in infested fields; not using seed grown on infested land for planting non-infested fields unless the seed has been properly cleaned; rotating infested fields and alternating host crops with non-host crops; using nematicides; and planting resistant plant varieties.

Methods have been proposed for the genetic transformation of plants in order to confer increased resistance to plant parasitic nematodes. U.S. Pat. Nos. 5,589,622 and 5,824,876 are directed to the identification of plant genes expressed specifically in or adjacent to the feeding site of the plant after attachment by the nematode. U.S. Pat. Nos. 5,589,622 and 5,824,876 disclose eight promoters isolated from potato roots infected with *Globodera rostochiensis*: no nematode-inducible promoters from other plant species are disclosed. These promoters are purported to be useful to direct the specific expression of toxic proteins or enzymes, or the expression of antisense RNA to a target gene or to general cellular genes.

U.S. Pat. No. 5,023,179 discloses a promoter enhancer element designated ASF-1, isolated from the CaMV promoter, which is purported to enhance plant gene expression in roots.

U.S. Pat. No. 5,750,386 discloses a deletion fragment of the RB7 root specific promoter of Nicotiana tabacum, which is purported to be nematode-responsive.

U.S. Pat. No. 5,837,876 discloses a root cortex specific gene promoter isolated from tobacco and designated TobRD2.

U.S. Pat. No. 5,866,777 discloses a two-gene approach to retarding formation of a nematode feeding structure. The first gene, barnase, is under control of a promoter that drives expression at least in the feeding structure. The second gene, barstar, is under control of a promoter that drives expression in all of the plant's cells except the feeding structure. Feeding site-specific promoters disclosed in U.S. Pat. No. 5,866,777 include truncated versions of the Δ0.3TobRB7 and roIC promoters.

U.S. Pat. No. 5,955,646 discloses chimeric regulatory regions based on promoters derived from the mannopine synthase and octopine synthase genes of Agrobacterium tumefaciens, which are purported to be nematode-inducible.

U.S. Pat. No. 6,005,092 discloses the N. tabacum endo-1, 4-β-glucanase (Ntce17) promoter.

U.S. Pat. Nos. 6,262,344 and 6,395,963 disclose promoters isolated from Arabidopsis thaliana, which are purported to be nematode-inducible.

U.S. Pat. No. 6,448,471 discloses a promoter from A. thaliana, which is specific for nematode feeding sites.

U.S. Pat. No. 6,593,513 discloses transformation of plants with barnase under control of the promoter of the A. thaliana endo-1,4-β-glucanase gene (cell) to produce plants capable of disrupting nematode attack.

U.S. Pat. No. 6,703,541 discloses cloning and isolation of maize peroxidase P7X gene and its promoter. The maize peroxidase P7X promoter is purported to be nematode inducible.

U.S. Pat. No. 6,906,241 discloses use of the Ntce17 promoter in combination with a heterologous nucleic acid that encodes a nematocidal or insecticidal protein.

U.S. Pat. No. 7,078,589 discloses cloning and isolation of the soybean Pyk20 gene and promoter, which are purported to be induced by SCN infection and to show strong activity in vascular tissues.

U.S. Pat. No. 7,196,247 discloses the promoter of soybean isoflavone synthase I, which is purported to be root specific and inducible in vegetative tissue by parasite attack.

U.S. Pat. No. 7,223,901 discloses a promoter from soybean phosphoribosylformylglycinamidine ribonucleotide synthase and deletion fragments thereof, which are purported to be responsive to nematode infection.

U.S. Patent Application Publication No. 2004/0078841 discloses promoter regions of the TUB-1, RPL16A, and ARSK1 promoters of Arabidopsis thaliana and the $PSMT_A$ promoter from Pisum sativum, all of which are purported to be root-specific.

U.S. Patent Application Publication No. 2004/0029167 discloses a promoter sequence of a class II caffeic acid 0-methyltransferase gene from tobacco, which is purported to be inducible in response to mechanical or chemical injury or to aggression by a pathogenic agent.

WO 94/10320 discloses the Δ0.3TobRB7 promoter fragment from tobacco and its use with a variety of genes for nematode feeding cell-specific expression.

WO 03/033651 discloses synthetic nematode-regulated promoter sequences designated SCP1, UCP3, and SUP.

WO 2004/029222 and its US counterpart U.S. Patent Application Publication No. 2005/0070697 disclose regulatory regions from the soybean adenosine-5'-phosphate deaminase and inositol-5-phosphatase genes, for use in improving nematode resistance in plants.

None of the above-mentioned root- or feeding-site specific promoters are currently in use in commercial seed containing an anti-nematode transgene. Although the need for such products has long been acknowledged, no one has thus far succeeded in developing nematode-resistant plants through recombinant DNA technology. A need continues to exist for root-specific and/or nematode feeding site-specific promoters to combine with transgenes encoding agents toxic to plant parasitic nematodes.

SUMMARY OF THE INVENTION

The invention provides promoter polynucleotides suitable for use in driving expression of a second polynucleotide in plant roots which are susceptible to attack by nematodes. The promoter polynucleotides of the invention are particularly useful for making agricultural crop plants resistant to infestation by nematodes.

In one embodiment, the invention provides a promoter comprising an isolated promoter polynucleotide, capable of mediating root-preferred and/or nematode-inducible expression, wherein the promoter polynucleotide is selected from the group consisting of a) a polynucleotide having the sequence as set forth in SEQ ID NO:1; b) a polynucleotide comprising nucleotides 476 to 1476 of a polynucleotide having the sequence as set forth in SEQ ID NO:1; c) a polynucleotide having at least 70% sequence identity to the polynucleotide of a) or b); d) a polynucleotide hybridizing under stringent conditions to the polynucleotide of a) or b); and e) a polynucleotide comprising a fragment of at least 50 consecutive nucleotides, or at least 100 consecutive nucleotides, or at least 200 consecutive nucleotides of a polynucleotide having the sequence as set forth in SEQ ID NO:1

The invention also relates to expression cassettes and transgenic plants which comprise the isolated promoter polynucleotides of the invention, and to methods of controlling parasitic nematode infestations in crops, wherein the methods employ recombinant nucleic acid constructs comprising the isolated promoter polynucleotides of the invention in operative association with a nucleic acid that encodes an agent that disrupts metabolism, growth, and/or reproduction of plant parasitic nematodes, that confers or improves plant resistance to plant parasitic nematodes, or that is toxic to plant parasitic nematodes to reduce crop destruction.

BRIEF DESCRIPTION OF THE DRAWINGS

FIG. 1: Nucleic acid sequence of promoter polynucleotide of Arabidopsis thaliana locus At5g12170 (SEQ ID NO:1).

FIG. 2: Nucleic acid sequence of Glycine max cDNA clone 50657480 (SEQ ID NO:2).

FIG. 3: Amino acid sequence encoded by Glycine max cDNA clone 50657480 (SEQ ID NO:3) where "*" indicates the stop codon.

FIG. 4: Microarray data of cDNA clone 50657480. The N in (N) denotes the number of cDNA microarray measurements and ND stands for non-detectable under experimental conditions described in this study. The designation "Untreated Root" means whole root tissue aRNA (amplified RNA) derived from uninfected root segments the same age as SCN inoculated segments. The designation "Non-Syncytia" means whole root tissue aRNA derived from SCN infected roots adjacent to the infected region which do not contain SCN or feeding sites. The designation "Syncytia" means aRNA SCN syncytia samples obtained using laser capture microdissection (LCM).

FIG. 5: Amino acid sequence encoded by *Arabidopsis thaliana* At5g12170 gene (SEQ ID NO: 4) where "*" indicates the stop codon.

FIG. 6: Alignment of amino acid sequence encoded by soybean cDNA clone 50657480 (SEQ ID NO: 3) with amino acid sequence encoded by *Arabidopsis thaliana* At5g12170 gene (SEQ ID NO: 4).

FIG. 7: β-glucuronidase expression patterns of binary vector pAW280 in the soybean hairy root assay set forth in Example 4. Soybean cyst nematode infected hairy roots and control uninfected hairy roots were stained 12 days after SCN inoculation. The following scoring index was used: "−" for no GUS staining, "+" for weak GUS staining, "++" for strong GUS staining, and "−/+" indicates that there were approximately 25% of the lines tested which had some vascular GUS staining in <25% of the root tissue observed.

FIG. 8: β-glucuronidase expression patterns of binary vectors pAW280, RTJ119, and RTJ120 in the soybean hairy root assay set forth in Example 7. Soybean cyst nematode infected hairy roots and control uninfected hairy roots were stained 12 days after SCN inoculation. The following scoring index was used: "−" for no GUS staining, "+" for weak GUS staining, "++" for strong GUS staining, and "−/+" indicates that there were approximately 25% of the lines tested which had some vascular GUS staining in <25% of the root tissue observed.

FIG. 9: Primer used for cloning of promoter polynucleotides

DETAILED DESCRIPTION OF PREFERRED EMBODIMENTS

The present invention may be understood more readily by reference to the following detailed description of the preferred embodiments of the invention and the examples included herein. Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement).

It is to be understood that as used in the specification and in the claims, "a" or "an" can mean one or more, depending upon the context in which it is used. Thus, for example, reference to "a cell" can mean that at least one cell can be utilized. It is to be understood that this invention is not limited to specific nucleic acids, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook and Russell, 2001 Molecular Cloning, Third Edition, Cold Spring Harbor, Plainview, N.Y.; Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York.

The promoter polynucleotides according to the present invention are provided in isolated and/or purified from their natural environment, in substantially pure or homogeneous form, or free or substantially free of other nucleic acids of the species of origin. An "isolated" nucleic acid as used herein is also substantially free—at the time of its isolation—of other cellular materials or culture medium when produced by recombinant techniques, or substantially free of chemical precursors when chemically synthesized. The promoter polynucleotides of the invention are isolated nucleic acids. Where used herein, the term "isolated" encompasses all of these possibilities.

The term "about" is used herein to mean approximately, roughly, around, or in the regions of. When the term "about" is used in conjunction with a numerical range, it modifies that range by extending the boundaries above and below the numerical values set forth. In general, the term "about" is used herein to modify a numerical value above and below the stated value by a variance of 10 percent, up or down (higher or lower).

The term "promoter" or promoter polynucleotide as used herein refers to a DNA sequence which, when ligated to a nucleotide sequence of interest, is capable of controlling the transcription of the nucleotide sequence of interest into mRNA. A promoter is typically, though not necessarily, located 5' (e.g., upstream) of a nucleotide of interest (e.g., proximal to the transcriptional start site of a structural gene) whose transcription into mRNA it controls, and provides a site for specific binding by RNA polymerase and other transcription factors for initiation of transcription. A "constitutive promoter" refers to a promoter that is able to express the open reading frame or the regulatory element that it controls in all or nearly all of the plant tissues during all or nearly all developmental stages of the plant. "Regulated promoter" refers to promoters that direct gene expression not constitutively, but in a temporally- and/or spatially manner, and includes both tissue-specific and inducible promoters. Different promoters may direct the expression of a gene or regulatory element in different tissues or cell types, or at different stages of development, or in response to different environmental conditions.

"Tissue-specific promoter" refers to regulated promoters that are not expressed in all plant cells but only in one or more cell types in specific organs (such as roots or seeds), specific tissues (such as embryo or cotyledon), or specific cell types (such as leaf parenchyma or seed storage cells). "Inducible promoter" refers to those regulated promoters that can be turned on in one or more cell types by an external stimulus, such as a chemical, light, hormone, stress, or a pathogen.

The term "nematode resistance" as used herein refers to the ability of a plant to avoid infection by nematodes, to kill nematodes or to hamper, reduce or stop the development, growth or multiplication of nematodes. This might be achieved by an active process, e.g. by producing a substance detrimental to the nematode or by a passive process, for example, by reducing nutrition for the nematode or inhibiting development of structures induced by the nematode such as syncytia or giant cells. The level of nematode resistance of a plant can be determined in various ways, e.g. by counting the nematodes able to establish parasitism on that plant after infection, or by measuring nematode stages of development present at various times after infection, or by measuring the proportion of male and female nematodes or the number of nematode eggs or cysts produced.

The term "sequence identity" or "identity" in the context of two polynucleotide or polypeptide sequences makes reference to those positions in the two sequences where identical pairs of symbols fall together when the sequences are aligned for maximum correspondence over a specified comparison window, for example, either the entire sequence as in a global alignment or the region of similarity in a local alignment. When percentage of sequence identity is used in reference to polypeptides it is recognized that residue positions that are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those skilled in the art. Typically this involves scoring a conservative substitution as a partial match rather than a mismatch, thereby increasing the percentage of sequence similarity.

As used herein, "percentage of sequence identity" or "sequence identity percentage" denotes a value determined by first noting in two optimally aligned sequences over a comparison window, either globally or locally, at each constituent position as to whether the identical nucleic acid base or amino acid residue occurs in both sequences, denoted a match, or if it does not, denoted a mismatch. As said alignments are constructed by optimizing the number of matching bases, while concurrently allowing both for mismatches at any position and for the introduction of arbitrarily-sized gaps, or null or empty regions where to do so increases the significance or quality of the alignment, the calculation determines the total number of positions for which the match condition exists, and then divides this number by the total number of positions in the window of comparison, and lastly multiplies the result by 100 to yield the percentage of sequence identity. "Percentage of sequence similarity" for protein sequences can be calculated using the same principle, wherein the conservative substitution is calculated as a partial rather than a complete mismatch. Thus, for example, where an identical amino acid is given a score of 1 and a non-conservative substitution is given a score of zero, a conservative substitution is given a score between zero and 1. The scoring of conservative substitutions can be obtained from amino acid matrices known in the art, for example, Blosum or PAM matrices.

Methods of alignment of sequences for comparison are well known in the art. The determination of percent identity or percent similarity (for proteins) between two sequences can be accomplished using a mathematical algorithm. Preferred, non-limiting examples of such mathematical algorithms are, the algorithm of Myers and Miller (Bioinformatics, 4(1):11-17, 1988), the Needleman-Wunsch global alignment (J. Mol. Biol., 48(3):443-53, 1970), the Smith-Waterman local alignment (J. Mol. Biol., 147:195-197, 1981), the search-for-similarity-method of Pearson and Lipman (PNAS, 85(8): 2444-2448, 1988), the algorithm of Karlin and Altschul (Altschul et al., J. Mol. Biol., 215(3):403-410, 1990; PNAS, 90:5873-5877, 1993). Computer implementations of these mathematical algorithms can be utilized for comparison of sequences to determine sequence identity or to identify homologs.

Commonly assigned U.S. Patent application Ser. No. 60/899,739, filed contemporaneously with U.S. Patent application Ser. No. 60/899,739, discloses and claims the soybean cDNA designated GM50657480 represented herein as SEQ ID NOs:2 and 3, As shown in Example 2, expression of GM50657480 is up-regulated in syncytia induced by SCN. As shown in FIG. 6, the amino acid sequence of GM50657480 (SEQ ID NO:3) shows significant alignment with the amino acid sequence of At5g12170 (SEQ ID NO:4), indicating that the two proteins are orthologs. As demonstrated in Example 4, when placed in operative association with a GUS reporter gene, the Arabidopsis promoter polynucleotide of the present invention (SEQ ID NO:1) is up-regulated in soybean hairy roots infected by nematodes.

The invention is therefore embodied in an isolated promoter polynucleotide having a sequence as set forth in SEQ ID NO:1, or a minimal promoter polynucleotide fragment derived from an isolated promoter polynucleotide having the sequence as set forth in SEQ ID NO:1 which fragment is capable of driving root-specific and/or nematode-inducible expression of a second polynucleotide. The term "equivalent fragment" or "minimal promoter polynucleotide fragment" as used herein refers to a fragment of a promoter polynucleotide that is able to mediate root-specific and/or nematode-inducible expression of a second polynucleotide. Equivalent fragments of a promoter polynucleotide of the invention can be obtained by removing non-essential functional elements without deleting the essential ones, e.g. essential transcription factor binding sites. Narrowing the promoter polynucleotide sequence to its essential, functional elements can be realized in vitro by trial-and-error deletion mutations, or in silico using promoter element search routines. Regions essential for promoter activity often demonstrate clusters of certain, known promoter elements. Such analysis can be performed using available computer algorithms such as PLACE ("Plant Cis-acting Regulatory DNA Elements"; Higo 1999), the BIOBASE database "Transfac" (Biologische Datenbanken GmbH, Braunschweig; Wingender 2001) or the database PlantCARE (Lescot 2002). Especially preferred are equivalent fragments of promoter polynucleotides, which are obtained by deleting the region encoding the 5'-untranslated region of the mRNA, thus only providing the (untranscribed) promoter polynucleotide region. The 5'-untranslated region can be easily determined by methods known in the art (such as 5'-RACE analysis). Accordingly, some of the promoter polynucleotides of the invention are equivalent fragments of other promoter polynucleotides. Specific minimal promoter polynucleotide fragments of the invention include, without limitation, a polynucleotide comprising nucleotides 476 to 1476 of a sequence as set forth in SEQ ID NO:1, a polynucleotide comprising a fragment of at least 50 consecutive nucleotides, or at least 100 consecutive nucleotides, or at least 200 consecutive nucleotides, or at least 300 consecutive nucleotides, or at least 400 consecutive nucleotides, or at least 500 consecutive nucleotides, of a promoter polynucleotide having the sequence as set forth in SEQ ID NO:1.

Alternatively, the promoter polynucleotide of the invention comprises an isolated polynucleotide which hybridizes under stringent conditions to a promoter polynucleotide having the sequence as set forth in SEQ ID NO:1, or to a minimal promoter polynucleotide fragment derived from the promoter polynucleotide having the sequence as set forth in SEQ ID NO:1. Stringent hybridization conditions as used herein are well known, including, for example, 400 mM NaCl, 40 mM PIPES pH 6.4, 1 mM EDTA, 60° C. hybridization for 12-16 hours; followed by washing in 0.1% SDS, 0.1% SSC at approximately 65° C. for about 15-60 minutes.

The invention is further embodied in an isolated polynucleotide that hybridizes under stringent conditions to a polynucleotide comprising nucleotides 476 to 1476 of a sequence as set forth in SEQ ID NO:1, wherein the promoter polynucleotide is capable of driving root-specific and/or nematode-inducible expression of a second polynucleotide and is induced in roots of a plant by plant parasitic nematodes. The promoter polynucleotide of the invention further comprises an isolated promoter polynucleotide which is at least 50-60%, or at least 60-70%, or at least 70-80%, 80-85%, 85%, 68%, 87%, 88%, 89%, 90%, 91%, 92%, 93%, 94%, or at least 95%, 96%, 97%, 98%, 99% or identical to a polynucleotide having a sequence as set forth in SEQ ID NO;1, or a minimal promoter polynucleotide fragment derived from the sequence set forth in SEQ ID NO:1, which promoter polynucleotide is capable of driving root-specific and/or nematode-inducible expression of a second polynucleotide. The length of the sequence comparison for polynucleotides is at least 50 consecutive nucleotides, or at least 100 consecutive nucleotides, or at least 200 consecutive nucleotides, or at least 500 consecutive nucleotides, up to the whole length of the sequence. In case the two sequences to be compared do not have an identical length, the term "the whole length of the sequence" refers to the whole length of the shorter sequence.

The methods disclosed herein may be employed to isolate additional minimal promoter polynucleotide fragments of SEQ ID NO:1 which are capable of mediating root-specific and/or nematode-inducible expression of a second polynucleotide. The invention further embodies "variants" or "derivatives" of the promoter polynucleotides of the invention. Derivatives of the specific promoter polynucleotide sequences and their specific elements may include, but are not limited to, deletions of sequence, single or multiple point mutations, alterations at a particular restriction enzyme site, addition of functional elements, or other means of molecular modification. This modification may or may not enhance, or otherwise alter the transcription regulating activity of said promoter polynucleotide. For example, one of skill in the art may delimit the functional elements e.g. promoter elements like, but not limited to, transcription factor binding sites, within the promoter polynucleotides and delete any non-essential functional elements. Functional elements may be modified or combined to increase the utility or the expression level of the promoter polynucleotides of the invention for any particular application.

As indicated above, deletion mutants of the promoter polynucleotide of the invention can also be randomly prepared and then assayed. With this strategy, a series of constructs are prepared, each containing a different portion of the promoter polynucleotide (a subclone), and these constructs are then screened for activity. A suitable means for screening for activity is to attach a promoter polynucleotide construct, which contains a promoter polynucleotide fragment to a selectable or screenable marker, and to isolate only those cells expressing the marker gene. In this way, a number of different, deleted promoter polynucleotide constructs are identified which still retain the desired, or even enhanced, activity. The smallest promoter polynucleotide fragment, which is required for activity, is thereby identified through comparison of the selected constructs. This promoter polynucleotide fragment may then be used for the construction of vectors for the expression of a second polynucleotide e.g. coding for exogenous genes.

The means for mutagenizing or creating deletions in a polynucleotide e.g. a promoter polynucleotide are well known to those of skill in the art and are disclosed, for example, in U.S. Pat. No. 6,583,338, incorporated herein by reference in its entirety. One example of a regulatory sequence variant is a promoter polynucleotide formed by one or more deletions from a larger promoter polynucleotide. The 5' portion of a promoter polynucleotide up to the TATA box near the transcription start site can sometimes be deleted without abolishing promoter activity, as described by Zhu et al., (1995) The Plant Cell 7:1681-1689. A routine way to remove part of a polynucleotide is to use an exonuclease in combination with DNA amplification to produce unidirectional nested deletions of double-stranded DNA clones. A commercial kit for this purpose is sold under the trade name Exo-Size™ (New England Biolabs, Beverly, Mass.). Biologically active variants also include, for example, the native promoter polynucleotides of the invention having one or more nucleotide substitutions, deletions or insertions.

Derivatives and variants also include homologs, paralogs and orthologs from other species, such as but not limited to, bacteria, fungi, and plants. "Homolog" is a generic term used in the art to indicate a polynucleotide or polypeptide sequence possessing a high degree of sequence relatedness to a reference sequence. Such relatedness may be quantified by determining the degree of identity and/or similarity between the two sequences as hereinbefore defined. Falling within this generic term are the terms "ortholog", and "paralog". "Paralog" refers to a polynucleotide or polypeptide that within the same species which is functionally similar. "Ortholog" refers to a polynucleotide or polypeptide that is the functional equivalent of the polynucleotide or polypeptide in another species. An orthologous gene means preferably a gene, which encodes an orthologous protein. More specifically, the term "ortholog" denotes a polypeptide or protein obtained from one species that is the functional counterpart of a polypeptide or protein from a different species. Sequence differences among orthologs are the result of speciation.

As used herein, the term "allelic variant" refers to a polynucleotide containing polymorphisms that lead to changes in the nucleotides of the polynucleotide and that exist within a natural population (e.g. in a plant species or variety). The term "allelic variant" also refers to a promoter polynucleotide containing polymorphisms that lead to changes in the polynucleotide sequence of a promoter polynucleotide and that exist within a natural population. Such natural allelic variations can typically result in 1-5% variance in a polynucleotide, or 1-5% variance in the encoded protein. Allelic variants can be identified by sequencing the polynucleotide of interest in a number of different plants, which can be readily carried out by using, for example, hybridization probes to identify the same promoter polynucleotide, gene or genetic locus in those plants. Any and all such nucleic acid variations in a promoter polynucleotide, which are the result of natural allelic variation and do not alter the functional activity of the promoter polynucleotide are intended to be within the scope of the invention. Allelic variants of a gene may be used to clone variants of the promoter polynucleotides of the invention. A variant of a promoter polynucleotide of the invention obtained this way may be at least 70%, 80%, 85%, 90%, 95%, 96%, 97%, 98%, 99% identical to the sequence of SEQ ID NO: 1 or to the sequence of nucleotides 476 to 1476 of SEQ ID NO:1 and are naturally connected to a gene coding for a polypeptide being at least 95%, 96%, 97%, 98%, 99% identical to a sequence as described by SEQ ID NO: 3 or SEQ ID NO: 4. Naturally connected means that both polynucleotides are part of a continuous polynucleotide occurring in nature, e.g. in a plant genome, wherein the polynucleotide stretch connecting both sequences is not longer than 3000 bp, 2000 bp, 1000 bp, 500 bp, 200 bp, 100 bp or 50 bp. Preferably the variant of a promoter polynucleotide of the invention is in the upstream region of an orthologous gene coding for a polypeptide having at least 95%, 96%, 97%, 98%, 99% identity to the sequence as described by SEQ ID NO: 3 or SEQ ID NO: 4.

In accordance with the invention, the isolated promoter polynucleotides of the present invention may be placed in operative association with a second polynucleotide for root-specific and/or nematode-inducible expression of the second polynucleotide in plants in order to vary the phenotype of that plant. As used herein, the terms "in operative association," "operably linked," and "associated with" are interchangeable and mean the functional linkage of a promoter and a second polynucleotide on a single polynucleotide fragment in such a way that the transcription of the second polynucleotide is initiated and mediated by the promoter. In general, nucleic acids that are in operative association are contiguous.

Any second polynucleotide may be placed in operative association with the promoter polynucleotides of the invention to effect root-specific or pathogen-inducible expression of the second polynucleotide. Second polynucleotides include, for example, an open reading frame, a portion of an open reading frame, a polynucleotide encoding a fusion protein, an anti-sense sequence, a sequence encoding a double-stranded RNA sequence, a transgene, and the like. The second polynucleotide may encode an insect resistance gene, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker gene, a positive selectable marker gene, a gene affecting plant agronomic characteristics (i.e., yield), an environmental stress resistance gene (as exemplified by genes imparting resistance or tolerance to drought, heat, chilling, freezing, excessive moisture, salt stress, or oxidative stress), genes which improve starch properties or quantity, oil quantity and quality, amino acid or protein composition, and the like.

Preferably, the second polynucleotide encodes a RNA, preferably a double-stranded RNA (dsRNA) or an antisence RNA, a siRNA, a miRNA or its precursor, and the like.

Preferably, the second polynucleotide encodes a RNA, preferably a double-stranded RNA (dsRNA), which is substantially identical or homologous in whole or in part to a plant gene or a plant promoter required for formation or maintenance of a nematode feeding site e.g. by destroying or hampering the development or integrity of syncytia or giant cells. In one embodiment the second polynucleotide encodes a dsRNA, an antisense RNA, a siRNA, a miRNA which is complementary to a plant promoter and leads to down regulation of the plant promoter. The second polynucleotide may alternatively encode an agent, e.g. a protein, a dsRNA, an antisense RNA, a siRNA, a miRNA or its precursor, that disrupts or hampers the growth and/or reproduction of plant parasitic nematodes, that confers or improves plant resistance to plant parasitic nematodes, or that is toxic to plant parasitic nematodes to reduce crop destruction. Any polynucleotide encoding an agent that disrupts the growth and/or reproduction of plant parasitic nematodes, that confers or improves plant resistance to plant parasitic nematodes, or that is toxic to plant parasitic nematodes may be employed in accordance with the invention. For example, the second polynucleotide may encode a double-stranded RNA that is substantially identical to a target gene of a parasitic plant nematode that is essential for metabolism, survival, metamorphosis, or reproduction of the nematode. The second polynucleotide may alternatively encode a double-stranded RNA that is substantially identical to a plant gene in the feeding sites of plant roots that is essential for the survival, growth or fertility of the nematode.

As used herein, taking into consideration the substitution of uracil for thymine when comparing RNA and DNA sequences, the terms "substantially identical" and "corresponding to" mean that the nucleotide sequence of one strand of the dsRNA is at least about 80%-90% identical to 20 or more contiguous nucleotides of the target gene, more preferably, at least about 90-95% identical to 20 or more contiguous nucleotides of the target gene, and most preferably at least about 95-99% identical or absolutely identical to 20 or more contiguous nucleotides of the target gene. Exemplary plant parasitic nematode target genes are set forth, for example, in commonly assigned co-pending U.S. Patent Application Publication No. 2005/188438, incorporated herein by reference. Alternatively, for nematode control, the second polynucleotide placed in operative association with the promoter polynucleotides of the invention may encode an open reading frame, preferably a protein coding gene. For example the second polynucleotide may encode any open reading frame from any species. Non limiting examples are open reading frames from a *Glycine, Arabidopsis, Medicago, Escherichia, Baccillus, Rhizobium* or *Saccharomyces* species. For example, the second nucleic acid may encode an insect resistance gene, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker gene, a positive selectable marker gene, a gene affecting plant agronomic characteristics (i.e., yield), an environmental stress resistance gene (as exemplified by genes imparting resistance or tolerance to drought, heat, chilling, freezing, excessive moisture, salt stress, or oxidative stress), genes which improve starch properties or quantity, oil quantity and quality, amino acid or protein composition, and the like. In one embodiment the open reading frame encodes a protein that when overexpressed in the feeding site results in increased nematode resistance. The molecular mechanism of nematode resistance can vary greatly depending on the particular strategy. As an example, increased nematode resistance can be achieved by overexpressing a gene that is toxic to a nematode, which disrupts the formation and/or maintenance of the nematode feeding site, modifies the availability or delivery of nutrients to the nematode, increases plant defense response, or is in any manner detrimental to nematode reproduction. In another embodiment the gene encodes a nematode-toxic protein. For example, polynucleotides encoding microbial toxins or fragments thereof, toxins or fragments thereof derived from insects such as those described in U.S. Pat. Nos. 5,457,178; 5,695,954; 5,763,568; 5,959,182; and the like, are useful in this embodiment of the invention.

Crop plants and corresponding pathogenic nematodes are listed in Index of Plant Diseases in the United States (U.S. Dept. of Agriculture Handbook No. 165, 1960); Distribution of Plant-Parasitic Nematode Species in North America (Society of Nematologists, 1985); and Fungi on Plants and Plant Products in the United States (American Phytopathological Society, 1989). For example, plant parasitic nematodes that are targeted by the present invention include, without limitation, cyst nematodes and root-knot nematodes. Specific plant parasitic nematodes which are targeted by the present invention include, without limitation, *Heterodera glycines, Heterodera schachtii, Heterodera avenae, Heterodera oryzae, Heterodera cajani, Heterodera trifolii, Heterodera zea, Globodera pallida, Globodera rostochiensis, Globodera tabacum, Meloidogyne incognita, Meloidogyne arenaria, Meloidogyne hapla, Meloidogyne javanica, Meloidogyne naasi, Meloidogyne exigua, Ditylenchus dipsaci, Ditylenchus angustus, Radopholus similis, Radopholus citrophilus, Helicotylenchus multicinctus, Pratylenchus coffeae, Pratylenchus brachyurus, Pratylenchus vulnus, Paratylenchus curvitatus, Paratylenchus zeae, Rotylenchulus reniformis, Paratrichodorus anemones, Paratrichodorus minor, Paratrichodorus christiei, Anguina tritici, Bidera avenae, Subanguina radicicola, Hoplolaimus seinhorsti, Hoplolaimus Columbus, Hoplolaimus galeatus, Tylenchulus semipenetrans, Hemicycliophora arenaria, Rhadinaphelenchus cocophilus, Belonolaimus longicaudatus, Trichodorus primitivus, Nacobbus aberrans, Aphelenchoides besseyi, Hemicriconemodes kanayaensis, Tylenchorhynchus claytoni, Xiphinema americanum, Cacopaurus pestis*, and the like.

In one embodiment, the targeted nematodes belong to nematode families inducing giant or syncytial cells. Nematodes inducing giant or syncytial cells belong to the families Longidoridae, Trichodoridae, Heterodidae, Meloidogynidae, Pratylenchidae or Tylenchulidae. In particular to the families Heterodidae and Meloidogynidae.

Accordingly, in another embodiment the targeted nematodes belong to one or more genus selected from the group of *Naccobus, Cactodera, Dolichodera, Globodera, Heterodera, Punctodera, Longidorus* or *Meloidogyne*. In a preferred embodiment the targeted nematodes belong to one or more genus selected from the group of *Naccobus, Cactodera, Dolichodera, Globodera, Heterodera, Punctodera* or *Meloidogyne*. In a more preferred embodiment the targeted nematodes belong to one or more genus selected from the group of *Globodera, Heterodera*, or *Meloidogyne*. In an even more preferred embodiment the targeted nematodes belong to one or both genus selected from the group of *Globodera* or *Heterodera*. In another embodiment the targeted nematodes belong to the genus *Meloidogyne*.

When the targeted nematodes are of genus *Globodera*, the species targeted may be selected from the group consisting of *G. achilleae, G. artemisiae, G. hypolysi, G. mexicana, G. millefolii, G. mali, G. pallida, G. rostochiensis, G. Tabacum*, and *G. virginiae*. In a preferred embodiment the targeted *Globodera* nematode includes at least one of the species *G. pallida, G. tabacum,* or *G. rostochiensis*. When the targeted nematode is of genus *Heterodera*, the species may be selected from the group consisting of *H. avenae, H. carotae, H. ciceri, H. cruciferae, H. delvii, H. elachista, H. filipjevi, H. gambiensis, H. glycines, H. goettingiana, H. graduni, H. humuli, H. hordecalis, H. latipons, H. major, H. medicaginis, H. oryzicola, H. pakistanensis, H. rosii, H. sacchari, H. schachtii, H. sorghi, H. trifolii, H. urticae, H. vigni* and *H. zeae*. In a preferred embodiment the targeted *Heterodera* nematodes include at least one of the species *H. glycines, H. avenae, H. cajani, H. gottingiana, H. trifolii, H. zeae* or *H. schachtii*. In a more preferred embodiment the targeted nematodes includes at least one of the species *H. glycines* or *H. schachtii*. In a most preferred embodiment the targeted nematode is the species *H. glycines*.

When the targeted nematodes are of the genus *Meloidogyne*, the targeted nematode may be selected from the group consisting of *M. acronea, M. arabica, M. arenaria, M. artiellia, M. brevicauda, M. camelliae, M. chitwoodi, M. cofeicola, M. esigua, M. graminicola, M. hapla, M. incognita, M. indica, M. inornata, M. javanica, M. lini, M. mali, M. microcephala, M. microtyla, M. naasi, M. salesi* and *M. thamesi*. In a preferred embodiment the targeted nematodes includes at least one of the species *M. javanica, M. incognita, M. hapla, M. arenaria* or *M. chitwoodi*.

Any plant species can be transformed with the promoter polynucleotides of the invention. For example, Plants which may be transformed with nucleic acid constructs containing the promoter polynucleotides of the present invention include, without limitation, plants from a genus selected from the group consisting of *Medicago, Lycopersicon, Brassica, Cucumis, Solanum, Juglans, Gossypium, Malus, Vitis, Antirrhinum, Populus, Fragaria, Arabidopsis, Picea, Capsicum, Chenopodium, Dendranthema, Pharbitis, Pinus, Pisum, Oryza, Zea, Triticum, Triticale, Secale, Lolium, Hordeum, Glycine, Pseudotsuga, Kalanchoe, Beta, Helianthus, Nicotiana, Cucurbita, Rosa, Fragaria, Lotus, Medicago, Onobrychis, trifolium, Trigonella, Vigna, Citrus, Linum, Geranium, Manihot, Daucus, Raphanus, Sinapis, Atropa, Datura, Hyoscyamus, Nicotiana, Petunia, Digitalis, Majorana, Ciahorium, Lactuca, Bromus, Asparagus, Antirrhinum, Heterocallis, Nemesis, Pelargonium, Panicum, Pennisetum, Ranunculus, Senecio, Salpiglossis, Browaalia, Phaseolus, Avena,* and *Allium*.

Derivatives and variants of the promoter polynucleotides can preferably be used in particular plant clades, families, genus or plant species. Derivatives and variants of the promoter polynucleotides which can be isolated from one plant species are preferably used in plants of the same clade, family, genus or species of plants of which the plant, used for isolation of the derivative and variant of the promoter polynucleotides, belongs to. Accordingly in one embodiment the plant is a monocotyledonous plant, preferably a plant of the family Poaceae, Musaceae, Liliacese or Bromeliaceae, preferably of the family Poaceae. Accordingly, in yet another embodiment the plant is a Poaceae plant of the genus *Zea, Triticum, Oryza, Hordeum. Secale, Avena, Saccharum, Sorghum, Pennisetum, Setaria, Panicum, Eleusine, Miscanthus, Brachypodium, Festuca* or *Lolium*. When the plant is of the genus *Zea*, the preferred species is *Z. mays*. When the plant is of the genus *Triticum*, the preferred species is *T. aestivum, T. speltae* or *T. durum*. When the plant is of the genus *Oryza*, the preferred species is *O. sativa*. When the plant is of the genus *Hordeum*, the preferred species is *H. vulgare*. When the plant is of the genus *Secale*, the preferred species *S. cereale*. When the plant is of the genus *Avena*, the preferred species is *A. sativa*. When the plant is of the genus *Saccarum*, the preferred species is *S. officinarum*. When the plant is of the genus *Sorghum*, the preferred species is *S. vulgare, S. bicolor* or *S. sudanense*. When the plant is of the genus *Pennisetum*, the preferred species is *P. glaucum*. When the plant is of the genus *Setaria*, the preferred species is *S. italica*. When the plant is of the genus *Panicum*, the preferred species is *P. milliaceum* or *P. virgatum*. When the plant is of the genus *Eleusine*, the preferred species is *E. coracana*. When the plant is of the genus *Miscanthus*, the preferred species is *M. sinensis*. When the plant is of the genus *Brachypodium*, the preferred species is *B. distachyon*. When the plant is a plant of the genus *Festuca*, the preferred species is *F. arundinaria, F. rubra* or *F. pratensis*. When the plant is of the genus *Lolium*, the preferred species is *L. perenne* or *L. multiflorum*. Alternatively, the plant may be *Triticosecale*.

Alternatively, in one embodiment the plant is a dicotyledonous plant, preferably a plant of the family Fabaceae, Solanaceae, Brassicaceae, Chenopodiaceae, Asteraceae, Malvaceae, Linacea, Euphorbiaceae, Convolvulaceae Rosaceae, Cucurbitaceae, Theaceae, Rubiaceae, Sterculiaceae or Citrus. In one embodiment the plant is a plant of the family Fabaceae, Solanaceae or Brassicaceae. Accordingly, in one embodiment the plant is of the family Fabaceae, preferably of the genus *Glycine, Pisum, Arachis, Cicer, Vicia, Phaseolus, Lupinus, Medicago* or *Lens*. Preferred species of the family Fabaceae are *M. truncatula, M. sativa, G. max, P. sativum, A. hypogea, C. arietnum, V. faba, P. vulgaris, Lupinus albus, Lupinus luteus, Lupinus angustifolius* or *Lens culinaris*. More preferred are the species *G. max* and *A. hypogea, M. sativa*. Most preferred is the species *G. max* When the plant is of the family Solanaceae, the preferred genus is *Solanum, Lycopersicon, Nicotiana* or *Capsicum*. Preferred species of the family Solanaceae are *S. tuberosum, L. esculentum, N. tabaccum* or *C. chisense*. More preferred is *S. tuberosum*. Accordingly, in one embodiment the plant is of the family Brassicaceae, preferably of the genus *Arabidopsis, Brassica* or *Raphanus*. Preferred species of the family Brassicaceae are the species *A. thaliana, B. napus, B. oleracea, B. juncea* or *B. rapa*. More preferred is the species *B. napus*. When the plant is of the family Chenopodiaceae, the preferred genus is *Beta* and the preferred species is the *B. vulgaris*. When the plant is of the family Asteraceae, the preferred genus is *Helianthus* and the preferred species is *H. annuus*. When the plant is of the family Malvaceae, the preferred genus is *Gossypium* or *Abelmoschus*. When the genus is *Gossypium*, the preferred species is *G. hirsutum* or *G. barbadense* and the most preferred species is *G. hirsutum*. A preferred species of the genus *Abelmoschus* is the species *A. esculentus*. When the plant is of the family Linacea, the preferred genus is *Linum* and the preferred species is *L. usitatissimum*. When the plant is of the family Euphorbiaceae, the preferred genus is *Manihot, Jatropa* or *Rhizinus* and the preferred species are *M. esculenta J. curcas,* or *R. comunis*. When the plant is of the family Convolvulaceae, the preferred genus is *Ipomea* and the preferred species is *I. batatas*. When the plant is of the family Rosaceae, the preferred genus is *Rosa, Malus, Pyrus, Prunus, Rubus, Ribes, Vaccinium* or *Fragaria* and the preferred species is the hybrid *Fragaria× ananassa*. When the plant is of the family Cucurbitaceae, the preferred genus is *Cucumis, Citrullus* or *Cucurbita* and the preferred species is *Cucumis sativus, Citrullus lanatus,* or *Cucurbita pepo*. When the plant is of the family Theaceae, the preferred genus is *Camellia* and the preferred species is *C. sinensis*. When the plant is of the family Rubiaceae, the preferred genus is *Coffea* and the preferred species is *C. arabica* or *C. canephora*. When the plant is of the family Sterculiaceae, the preferred genus is *Theobroma* and the preferred species is *T. cacao*. When the plant is of the genus *Citrus*, the preferred species is *C. sinensis, C. limon, C. reticulate, C. maxima*, and hybrids of *Citrus* species, or the like.

In another embodiment, the promoter polynucleotide is induced in roots of a plant exposed to a nematode stimulus. A nematode stimulus can be present when the plant is infected or is in the process of becoming infected by plant parasitic nematodes. A promoter polynucleotide mediating expression in response to a nematode stimulus is also called a nematode-inducible promoter polynucleotide. The term root-preferred expression in regard to promoters, promoter polynucleotides, isolated nucleic acids or polynucleotides of the invention means expression mainly in root-tissue, in particular in root vascular tissue. Expression mainly in root-tissue means, that the amount of mRNA produced under control of the promoter polynucleotide of the invention is at least 10 times, 50 times, 100 times or 200 times higher in a particular amount of root-tissue when compared to the amount of mRNA produced in the same amount of other tissue, e.g. leaf, stem or flower tissue.

The invention is also embodied in expression cassettes comprising the promoter polynucleotides of the invention. "Expression cassette" in this context is to be understood broadly as comprising all sequences contained in the cassette which may influence transcription of a nucleic acid of interest and, if applicable, translation thereof. In addition to the promoter polynucleotides of the invention, the expression cassette of the invention may further comprise regulatory elements that improve the function of the promoter polynucleotides or genetic elements that allow transcription and/or translation in prokaryotic and/or eukaryotic organisms, and downstream (in 3'-direction) regulatory elements such as a transcription termination sequence and a polyadenylation sequence. The various components of the expression cassette of the invention are sequentially and operably linked together.

Accordingly, an expression cassette of the invention may comprise a promoter comprising a promoter polynucleotide, capable of mediating root-preferred and/or nematode-inducible expression, wherein the promoter polynucleotide is selected from the group of polynucleotides consisting of a) a polynucleotide having the sequence as set forth in SEQ ID NO:1; b) a polynucleotide comprising nucleotides 476 to 1476 of a polynucleotide having the sequence as set forth in SEQ ID NO:1; c) a polynucleotide having at least 70% sequence identity to the polynucleotide of a) or b); d) a polynucleotide hybridizing under stringent conditions to the polynucleotide of a) or b); and e) a polynucleotide comprising a fragment of at least 50 consecutive nucleotides, or at least 100 consecutive nucleotides, or at least 200 consecutive nucleotides of a polynucleotide having the sequence as set forth in SEQ ID NO:1. In another embodiment, the promoter is induced in roots of a plant infected by plant parasitic nematodes.

Specific genetic elements that may optionally be included in the expression cassette of the invention include, without limitation, origins of replication to allow replication in bacteria, e.g., the ORI region from pBR322 or the P15A on; or elements required for *Agrobacterium* T-DNA transfer, such as, for example, the left and/or right borders of the T-DNA. Other components of the expression cassette of the invention may include, without limitation, additional regulatory elements such as, for example, enhancers, introns, polylinkers, multiple cloning sites, operators, repressor binding sites, transcription factor binding sites, and the like. Exemplary enhancers include elements from the CaMV 35S promoter, octopine synthase genes (Ellis el al., 1987), the rice actin I gene, the maize alcohol dehydrogenase gene (Callis 1987), the maize shrunken I gene (Vasil 1989), TMV Omega element (Gallie 1989) and promoters from non-plant eukaryotes (e.g.

yeast; Ma 1988). Exemplary plant intron sequences include introns from Adh1, bronze1, actin1, actin 2 (WO 00/760067), or the sucrose synthase intron; see: The Maize Handbook, Chapter 116, Freeling and Walbot, Eds., Springer, New York (1994).

Viral leader sequences may also enhance transcription of nucleic acids of interest by the expression cassette of the invention. For example, leader sequences from Tobacco Mosaic Virus (TMV), Maize Chlorotic Mottle Virus (MCMV), and Alfalfa Mosaic Virus (AMV) have been shown to be effective in enhancing expression. Other leaders known in the art include but are not limited to: Picornavirus leaders, for example, (Encephalomyocarditis virus (EMCV) leader; Potyvirus leaders, Tobacco Etch Virus (TEV) leader; MDMV leader (Maize Dwarf Mosaic Virus); Human immunoglobulin heavy-chain binding protein (BiP) leader, Untranslated leader from the coat protein mRNA of alfalfa mosaic virus (AMV RNA 4).

The expression cassette of the invention also comprises a transcription termination element or polyadenylation signal. Exemplary transcription termination elements include those from the nopaline synthase gene of *A. tumefaciens* (Bevan 1983), the terminator for the T7 transcript from the octopine synthase gene of *A. tumefaciens*, and the 3' end of the protease inhibitor I or II genes from potato or tomato.

A second polynucleotide to be transcribed into RNA, and, optionally, expressed as a protein is inserted into the expression cassette of the invention for transformation into an organism. In accordance with the invention, the second polynucleotide sequence is placed downstream (i.e., in 3'-direction) of the promoter polynucleotide of the invention and upstream of the transcription termination elements, in covalent linkage therewith. Preferably, the distance between the second polynucleotide sequence and the promoter polynucleotide of the invention is not more than 200 base pairs, more preferably not more than 100 base pairs, most preferably not more than 50 base pairs.

An expression cassette of the invention may also be assembled by inserting a promoter polynucleotide of the invention into the plant genome. Such insertion will result in an operable linkage to a nucleic acid sequence of interest native to the genome. Such insertions allow the nucleic acid of interest to be expressed or over-expressed preferentially in root tissue, after induction by nematodes, as the result of the transcription regulating properties of the promoter polynucleotide of the invention. The insertion may be directed or by chance. Preferably, the insertion is directed and realized, for example, by homologous recombination. By this procedure a natural promoter may be replaced in total or in part by the promoter polynucleotide of the invention, thereby modifying the expression profile of an endogenous gene.

The expression cassette of the invention may be inserted into a recombinant vector, plasmid, cosmid, YAC (yeast artificial chromosome), BAC (bacterial artificial chromosome), or any other vector suitable for transformation into a host cell. Preferred host cells are bacterial cells, in particular bacterial cells used for cloning or storing of polynucleotides or used for transformation of plant cells, such like, but not limited to, *Escherichia coli*, *A. tumefaciens* and *A. rhizogenes* cells, and plant cells. When the host cell is a plant cell, the expression cassette or vector may become inserted into the genome of the transformed plant cell. Alternatively, the expression cassette or vector may be maintained extra chromosomally. The expression cassette or vector of the invention may be present in the nucleus, chloroplast, mitochondria, and/or plastid of the cells of the plant. Preferably, the expression cassette or vector of the invention is inserted into the chromosomal DNA of the plant cell nucleus.

The expression cassette of the invention may be transformed into a plant to provide a transgenic plant comprising one or more polynucleotides in operative association with a promoter polynucleotide of the invention. The transgenic plant of this embodiment comprises a promoter comprising a promoter polynucleotide sequence as set forth in SEQ ID NO:1 or a minimal promoter polynucleotide fragment of SEQ ID NO:1. Alternatively, the transgenic plant of the invention comprises a promoter polynucleotide capable of mediating root-preferred and/or nematode-inducible expression that hybridizes under stringent conditions to a promoter polynucleotide having a sequence as set forth in SEQ ID NO:1, or a minimal promoter polynucleotide fragment of SEQ ID NO:1. Further, the transgenic plant of the invention comprises a promoter polynucleotide capable of mediating root-preferred and/or nematode-inducible expression having at least 70% sequence identity to a promoter polynucleotide having the sequence as set forth in SEQ ID NO:1, or a minimal promoter polynucleotide fragment of SEQ ID NO:1.

The term "plant" as used herein can, depending on context, be understood to refer to whole plants, plant cells, plant organs, harvested seeds, and progeny of same. The word "plant" also refers to any plant, particularly, to seed plants, and may include, but not limited to, crop plants. Plant parts or plant organs include, but are not limited to, stems, roots, shoots, fruits, ovules, stamens, leaves, embryos, meristematic regions, callus tissue, gametophytes, sporophytes, pollen, microspores, hypocotyls, cotyledons, anthers, sepals, petals, pollen, non-harvested seeds and the like. Harvested seeds refers to seeds, which are removed from the plant producing the seeds, while non-harvested seeds refer to seeds still connected to the plant producing the seeds e.g. being in the state of growing or ripening. The plant may be a monocot or a dicot. The plant can be from a genus selected from the group consisting of maize, wheat, barley, sorghum, rye, triticale, rice, sugarcane, citrus trees, pineapple, coconut, banana, coffee, tea, tobacco, sunflower, pea, alfalfa, soybean, carrot, celery, tomato, potato, cotton, tobacco, eggplant, pepper, oilseed rape, canola, beet, cabbage, cauliflower, broccoli, lettuce, *Lotus* sp., *Medicago truncatula*, prerennial grass, ryegrass, *Arabidopsis thaliana* and the like.

The transgenic plants of the invention are made using transformation methods known to those of skill in the art of plant biotechnology. Any method may be used to transform the recombinant expression vector into plant cells to yield the transgenic plants of the invention. Suitable methods for transforming or transfecting host cells including plant cells can be found, for example, in WO2006/024509 (PCT/EP2005/009366; U.S. Ser. No. 60/6060789) and in Sambrook et al. supra, and in other laboratory manuals such as Methods in Molecular Biology, 1995, Vol. 44, *Agrobacterium* protocols, Ed: Gartland and Davey, Humana Press, Totowa, N.J. General methods for transforming dicotyledenous plants are also disclosed, for example, in U.S. Pat. Nos. 4,940,838; 5,464,763, and the like. Methods for transforming specific dicotyledenous plants, for example, cotton, are set forth in U.S. Pat. Nos. 5,004,863; 5,159,135; and 5,846,797. Soybean transformation methods are set forth in U.S. Pat. Nos. 4,992,375; 5,416,011; 5,569,834; 5,824,877; 6,384,301 and in EP 0301749B1. Other plant transformation methods are disclosed, for example, in U.S. Pat. Nos. 4,945,050; 5,188,958; 5,596,131; 5,981,840, and the like.

Transformation methods may include direct and indirect methods of transformation. Suitable direct methods include polyethylene glycol induced DNA uptake, liposome-mediated transformation (U.S. Pat. No. 4,536,475), biolistic methods using the gene gun (Fromm M E et al., Bio/Technology. 8(9):833-9, 1990; Gordon-Kamm et al. Plant Cell 2:603, 1990), electroporation, incubation of dry embryos in DNA-comprising solution, and microinjection. In the case of these direct transformation methods, the plasmids used need not meet any particular requirements. Simple plasmids, such as those of the pUC series, pBR322, M13mp series, pACYC184 and the like can be used. If intact plants are to be regenerated from the transformed cells, an additional selectable marker gene is preferably located on the plasmid. The direct transformation techniques are equally suitable for dicotyledonous and monocotyledonous plants. Transformation can also be carried out by bacterial infection by means of *Agrobacterium* (for example EP 0 116 718), viral infection by means of viral vectors (EP 0 067 553; U.S. Pat. No. 4,407,956; WO 95/34668; WO 93/03161) or by means of pollen (EP 0 270 356; WO 85/01856; U.S. Pat. No. 4,684,611). *Agrobacterium* based transformation techniques (especially for dicotyledonous plants) are well known in the art. The *Agrobacterium* strain (e.g., *Agrobacterium tumefaciens* or *Agrobacterium rhizogenes*) comprises a plasmid (Ti or Ri plasmid) and a T-DNA element which is transferred to the plant following infection with *Agrobacterium*. The T-DNA (transferred DNA) is integrated into the genome of the plant cell. The T-DNA may be localized on the Ri- or Ti-plasmid or is separately comprised in a so-called binary vector. Methods for the *Agrobacterium*-mediated transformation are described, for example, in Horsch R B et al. (1985) Science 225:1229. The *Agrobacterium*-mediated transformation is best suited to dicotyledonous plants but has also been adapted to monocotyledonous plants. The transformation of plants by Agrobacteria is described in, for example, White F F, Vectors for Gene Transfer in Higher Plants, Transgenic Plants, Vol. 1, Engineering and Utilization, edited by S. D. Kung and R. Wu, Academic Press, 1993, pp. 15-38; Jenes B et al. Techniques for Gene Transfer, Transgenic Plants, Vol. 1, Engineering and Utilization, edited by S. D. Kung and R. Wu, Academic Press, 1993, pp. 128-143; Potrykus (1991) Annu Rev Plant Physiol Plant Molec Biol 42:205-225. Transformation may result in transient or stable transformation and expression. Although a nucleotide sequence of the present invention can be inserted into any plant and plant cell falling within these broad classes, it is particularly useful in crop plant cells.

The transgenic plants of the invention may be crossed with similar transgenic plants or with transgenic plants lacking genes operably associated with the promoter polynucleotide of the invention or with non-transgenic plants, using known methods of plant breeding, to prepare seed. Further, the transgenic plant of the present invention may comprise, and/or be crossed to another transgenic plant that comprises, one or more different genes operably linked to a promoter polynucleotide of the present invention or to another promoter, thus creating a "stack" of transgenes in the plant and/or its progeny. The seed is then planted to obtain a crossed fertile transgenic plant comprising the nucleic acid of interest and the promoter polynucleotide of the invention. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants. The seeds of this invention can be harvested from fertile transgenic plants and be used to grow progeny generations of transformed plants of this invention including hybrid plant lines comprising the DNA construct.

"Gene stacking" can also be accomplished by transferring two or more polynucleotides into the cell nucleus by plant transformation. In this context "gene" refers both to polynucleotides that encode a full-length protein and polynucleotides that encode an RNAi construct or a domain of a full-length protein. Multiple polynucleotides may be introduced into the cell nucleus during transformation either sequentially or in unison. Multiple plant genes or target pathogen genes can be down-regulated by gene silencing mechanisms, specifically RNAi, by using a single transgene targeting multiple linked partial sequences of interest. Stacked, multiple genes under the control of individual promoters can also be over-expressed to attain a desired single or multiple phenotype. Constructs containing gene stacks of both over-expressed genes and silenced targets can also be introduced into plants yielding single or multiple agronomically important phenotypes. In certain embodiments the nucleic acid sequences of the present invention can be stacked with any combination of polynucleotide sequences of interest to create desired phenotypes. The combinations can produce plants with a variety of trait combinations including but not limited to disease resistance, herbicide tolerance, yield enhancement, cold and drought tolerance. These stacked combinations can be created by any method including but not limited to cross breeding plants by conventional methods or by genetic transformation. If the traits are stacked by genetic transformation, the polynucleotide sequences of interest can be combined sequentially or simultaneously in any order. For example if two genes are to be introduced, the two sequences can be contained in separate transformation cassettes or on the same transformation cassette. The expression of the sequences can be driven by the same or different promoters.

The invention further comprises a crop comprising a plurality of the transgenic plants of the invention, planted together in an agricultural field.

The transgenic plants of the invention may be used in a method of controlling a plant parasitic nematode infestation in a crop, which comprises the step of growing said crop from seeds comprising an expression cassette comprising a plant promoter polynucleotide of the invention in operative association with a second nucleic acid that encodes an agent that disrupts the metabolism, growth and/or reproduction of said plant parasitic nematode, that improves plant tolerance to said plant parasitic nematode, or that is toxic to said plant parasitic nematode, wherein the expression cassette is stably integrated into the genomes of plant cells, plants and/or seeds. Such agents include, without limitation, a double-stranded RNA which is substantially identical to a target gene of a parasitic plant nematode which is essential for survival, metamorphosis, or reproduction of the nematode; a double-stranded RNA which is substantially identical to a plant gene required to maintain a nematode feeding site; an anti-sense RNA, an siRNA, an miRNA or its precursor, a protein that interferes with the metabolism, survival, metamorphosis or reproduction of the nematode, or a microbial toxin, a toxin derived from an insect, or any toxin that interferes with the metabolism, survival, metamorphosis or reproduction of the nematode, and the like.

The following examples are not intended to limit the scope of the claims to the invention, but are rather intended to be exemplary of certain embodiments. Any variations in the exemplified methods that occur to the skilled artisan are intended to fall within the scope of the present invention.

Example 1

Cloning a SCN-Inducible Promoter from *Arabidopsis*

*Arabidopsis* (Columbia ecotype) genomic DNA was extracted. The 1,476 bp (SEQ ID NO:1) genomic DNA region (putative promoter sequence) directly upstream of the ATG codon including 5'-untranslated region corresponding to *Arabidopsis* locus identifier At5g12170 was cloned using standard PCR amplification protocols. The 1,476 bp DNA fragment corresponding to the promoter regions of At5g12170 is shown as SEQ ID NO:1. PLACE (National Institute of Agrobiological Sciences, Ibaraki, Japan) analysis results indicate a TATA box is not present in SEQ ID NO:1 in the region 300 bp upstream of the 3' end of the promoter sequence.

Example 2

Cloning of At5g12170-Like Gene from Soybean

*Glycine max* cv. Williams 82 was germinated on agar plates for three days and then transferred to germination pouches. One day later, each seedling was inoculated with second stage juveniles (J2) of *H. glycines* race 3. Six days after inoculation, new root tissue was sliced into 1 cm long pieces, fixed, embedded in a cryomold, and sectioned using known methods. Syncytia cells were identified by their unique morphology of enlarged cell size, thickened cell wall, and dense cytoplasm and dissected into RNA extraction buffer using a PALM microscope (P.A.L.M. Microlaser Technologies GmbH, Bernried, Germany).

Total cellular RNA was extracted, amplified, and fluorescently labeled using known methods. As controls, total RNA was isolated from both "non-syncytia" and untreated control roots subjected to the same RNA amplification process. The amplified RNA was hybridized to proprietary soybean cDNA arrays. The table in FIG. 4 summarizes the expression data as measured by cDNA microarray analysis for this gene across all three cell/tissue samples: Syncytia, SCN infected non-syncytia, and untreated control root tissues. Relative levels of gene expression are shown as normalized signal intensities (±standard deviation). As demonstrated in FIG. 4, Soybean cDNA clone GM50657480 was identified as being up-regulated in syncytia of SCN-infected soybean roots. FIG. 3 depicts the amino acid sequence of soybean cDNA clone GM50657480 (SEQ ID NO:3). The GM50657480 cDNA sequence (SEQ ID NO:2) was determined not to be full-length as there is no ATG start codon and based on the alignment of the amino acid sequence of GM50657480 (SEQ ID NO: 3) to the amino acid sequence of At5g12170 (SEQ ID NO:4) shown in FIG. 6.

Example 3

Transgenic Hairy Root Assay of Full-Length Promoter Activity

To evaluate the expression activity of the cloned promoter, nucleotides 1-1476 of SEQ ID NO:1 were cloned upstream of a GUS reporter gene (bacterial R-glucuronidase or GUS gene (Jefferson (1987) EMBO J. 6, 3901-3907) to create the binary vector "pAW280". The plant selectable marker in the binary vector is a herbicide-resistant form of the acetohydroxy acid synthase (AHAS) gene from *A. thaliana* driven by the native *A. thaliana* AHAS promoter (Sathasivan et al., Plant Phys. 97:1044-50, 1991).

Binary vector pAW280 was transformed into *A. rhizogenes* K599 strain by electroporation (Cho et al., (1998) Plant Sci. 138, 53-65). Prior to *A. rhizogenes* inoculation, seeds from *G. max* Williams 82 (SCN-susceptible) were germinated, cotyledons were excised, and the adaxial side was wounded several times. An *A. rhizogenes* suspension was inoculated onto the wounded surface, and the inoculated cotyledon was incubated with the adaxial side up for three days at 25° C. under 16 hour/day lighting. The cotyledons were then transferred onto MS plates containing carbenicillin (to suppress *A. rhizogenes* growth) and 1 µM ARSENAL (imazapyr, BASF Corporation, Florham Park, N.J.) as the selection agent. Hairy roots were induced from the wounding site after two weeks. The roots resistant to ARSENAL and growing on the selection media were harvested and transferred onto fresh selection media of the same composition and incubated at 25° C. in darkness. Two weeks after harvesting hairy roots and culturing them on selection media, the hairy roots were subcultured onto MS media containing carbenicillin but not ARSENAL.

Several independent transgenic hairy root lines were generated from transformation with pAW280. Approximately three weeks after subculturing, the transgenic hairy-root lines were inoculated with *H. glycines* race 3 J2. Twelve days after *H. glycines* inoculation (DAI), the hairy roots were harvested and assayed for β-glucuronidase activity of the GUS gene using 5-bromo-4-chloro-3-indoyl-β-D-glucuronic acid (x-Gluc). At each time point after inoculation, a non-inoculated control plate from each line was also stained in GUS staining solution. The roots were then observed under a microscope for detection of GUS expression. For each transgenic line, 10 randomly picked syncytia were observed and scored for intensity of GUS expression. The following scoring index was used: "−" for no staining, "+" for weak staining, "++" for strong staining. A round-up average of the 10 counts was used to determine the GUS expression level in the syncytia for that line. In addition, GUS expression level in the same lines for other root tissues such as callus, root-tip, vasculature, cortical and primordial were also recorded using the same GUS scoring index of "−" for no staining, "−/+" indicates that there were approximately 25% of the lines tested showing vascular GUS staining in less than 25% of the root tissue observed, "+" for weak staining, "++" for strong staining. The results for lines transformed with pAW280 are presented in FIG. 7. The result of the GUS staining indicates that for most lines tested, the promoter fragment in pAW280 showed strong GUS expression in the syncytia at 12 DAI. In contrast, GUS expression in other root parts such as root tips, vascular tissue, and root cortex was undetected, highly variable between lines, or weak.

Example 4

Transgenic Hairy Root Assay of Minimal Promoter Fragments

A 1001 bp promoter deletion fragment represented by bases 476 to 1476 of SEQ ID NO:1 and a 500 bp promoter deletion fragment represented by bases 977 to 1476 of SEQ ID NO:1 were amplified from pAW280 using primers based on SEQ ID NO:1 and a standard PCR amplification protocol. The amplified DNA fragment size for each PCR product was verified by standard agarose gel electrophoresis and the DNA extracted from gel by Qiagen Gel Extraction Kit (Qiagen, Hilden, Germany). The promoter deletions derived from SEQ ID NO:1 were cloned upstream of the GUS reporter gene to create the binary vectors "RTJ119" and "RTJ120", respectively. The plant selection marker in the binary vectors was the mutated AHAS gene driven by the *Arabidopsis* AHAS promoter described in Example 3. Binary vectors pAW280, RTJ119 and RTJ120 were transformed into *A. rhizogenes* K599 strain to generate transgenic hairy roots as described in Example 3. The transgenic hairy root lines were inoculated with *H. glycines* SCN race 3 J2 and GUS expression was assayed as described in Example 3.

The results for lines transformed with pAW280, RTJ119, and RTJ120 are presented in FIG. 8. The 1001 bp minimal promoter fragment of SEQ ID NO:1 contained in RTJ119 conferred nematode-induced expression in syncytia. The intensity of syncytia staining in RTJ119 was not as strong as observed in pAW280. The 500 bp fragment of SEQ ID NO:1 contained in RTJ120 did not confer nematode-induced expression in syncytia.

Example 5

Whole Plant GUS Staining

Transgenic soybean whole plants are generated containing the promoter sequences represented by SEQ ID NO:1 or its variants in operative association with the GUS reporter gene by transforming representative constructs to characterize promoter expression in response to nematode infection in roots and whole plant tissues throughout the plant life cycle. Representative methods of promoter characterization in soybean whole plants include but are not limited to the following descriptions. Transgenic soybean T1 seeds are tested for zygosity and single copy events are germinated, grown in greenhouse conditions, and sampled for GUS expression at various stages of development in leaf, stem, flower, embryo, and seed pod tissues. In addition, root tissues are harvested at various times before and after SCN infection in inoculated and un-inoculated control roots. Multiple plants are tested for each event to determine consistent trends in the GUS staining analysis. Harvested samples are excised from the plant and assayed for GUS expression as described in Example 3. The tissues are then observed and scored for the intensity of GUS staining.

What is claimed is:

1. An expression cassette comprising an isolated promoter polynucleotide selected from the group consisting of:
   a) a polynucleotide comprising nucleotides 1 to 1476 of SEQ ID NO:1; and
   b) a polynucleotide comprising nucleotides 476 to 1476 of SEQ ID NO:1; said isolated promoter polynucleotide being operably linked to a second heterologous polynucleotide selected from the group consisting of an open reading frame, a portion of an open reading frame, a polynucleotide encoding a fusion protein, an anti-sense sequence, a sequence encoding a double-stranded RNA sequence, and a transgene.

2. The expression cassette of claim 1, wherein the second heterologous polynucleotide confers to a plant a trait selected from the group consisting of increased yield, increased survival under stress conditions, increased nutritional quality, increased resistance to a plant parasitic nematode, modified protein content, and modified oil content.

3. The expression cassette of claim 2, wherein the second heterologous polynucleotide confers increased resistance to a plant parasitic nematode by encoding:
   a) an agent that disrupts metabolism, growth, or reproduction of the plant parasitic nematode; or
   b) an agent that is toxic to the plant parasitic nematode.

4. A transgenic plant transformed with an expression cassette comprising an isolated promoter polynucleotide operably linked to a second heterologous polynucleotide, wherein the isolated promoter polynucleotide is selected from the group of consisting of:
   a) a polynucleotide comprising nucleotides 1 to 1476 of SEQ ID NO:1; and
   b) a polynucleotide comprising nucleotides 476 to 1476 of SEQ ID NO:1.

5. The plant of claim 4, wherein the plant is a monocot.

6. The plant of claim 4, wherein the plant is a dicot.

7. The plant of claim 4, wherein the plant is selected from the group consisting of maize, wheat, barley, sorghum, rye, triticale, rice, sugarcane, citrus trees, pineapple, coconut, banana, coffee, tea, tobacco, sunflower, pea, alfalfa, soybean, carrot, celery, tomato, potato, cotton, tobacco, eggplant, pepper, oilseed rape, canola, beet, cabbage, cauliflower, broccoli, lettuce, *Lotus* sp., *Medicago truncatula*, perennial grass, ryegrass, and *Arabidopsis thaliana*.

8. The plant of claim 4, wherein the isolated promoter polynucleotide comprises nucleotides 1 to 1476 of SEQ ID NO:1.

9. The plant of claim 4, wherein the isolated promoter polynucleotide comprises nucleotides 476 to 1476 of SEQ ID NO:1.

* * * * *

SEQUENCE LISTING

```
<160> NUMBER OF SEQ ID NOS: 9

<210> SEQ ID NO 1
<211> LENGTH: 1476
<212> TYPE: DNA
<213> ORGANISM: Arabidopsis thaliana

<400> SEQUENCE: 1
gctcgcgtta gttccactca aggagtatcc tttcttcctt gcgcaactct ccaccttcgg      60
gtaaagtacc atctctagca tcttgagtct tgatcaactt ctgttttgct tactctcaaa     120
atgcattaat tttttttat actagatcat agtattatat ctcttaatct acctattgaa     180
atctacttaa tgttttact aaaacctacg tgtttctctt tagagaattt tgtgctatgc     240
atgaattaga ggttagtaat gtgtaatact tcataagtct agatttattt gttggttaac     300
acgtttagta attcacacac acacaccacc ttagatattt tactgtgaat tagaaaaaga     360
tacatagtta ggagtgtttt tttaaaaaaa ttcaatcatg agaaaattag aggtgtgatg     420
ttatacatta tgaaaatgca aagggcagat acgaataaat tagaaacttg tttaacgggt     480
cagagttggc ttctagtctc tttcgacttg gatacttctt cttctacaat tgggacatta     540
ttgtaggcgc attatatcat ttctctacat gcaatgaatg tacatacatt aattcacatt     600
tatttttgga ataatcatat gagtgatcga agtttgtatt tatatattca atcttcacaa     660
actactttta tttaaaaatc atttgcaaaa tgctatttta ttgacaaaaa gatatatgct     720
ataaaataaa ataaaattca caaactatag tcattaatac aaaaagaaat cattgaatat     780
ggtagagggg aaacaaaaaa aaaacacgac gatgtaagtt ggtggaacca cattatcaaa     840
ataaaagaag gtggtggaac caaattgaat aaagtccgtc catatcatta tccgtccctt     900
aggagcctct aattagtaat attcttatgg gtccactgtg gcttagagga cttgattaaa     960
accattctta tttagtgcta actttgtgag ggttggaata acgaaccaag ctgattcaaa    1020
ccattccaaa acaaagttgt cacatatttc aaaaccaaag tttaccggac agagaaatat    1080
ggtgtgtttt tctcaaacca agctaaatgg aatccattgt aaaccaaaat gttcacacct    1140
acctattctt ttggagtccc ttttccatgt gtttgctgtc tgctagtcaa gtttcattag    1200
ctgattgcct tgcatcatat tcttggatca actttttttt tttttttttt tggggtaatt    1260
aacaaaatgc ttaaatttct caagactata ggatcacatt acctgtgtgc ttaacataac    1320
ttttagatag gctagagaat tgatctatta caagataatc aataatttac agaagaaaac    1380
```

```
attctttttt ttgttctatt tccttcatgt aggtatgtag ctgtatatta tactatcttg   1440
tattttcgat atcgtgctgg aactgtcaca gatgca                             1476
```

<210> SEQ ID NO 2
<211> LENGTH: 647
<212> TYPE: DNA
<213> ORGANISM: Glycine max

<400> SEQUENCE: 2

```
aagatggtgc agcctgcttc ctaaattttg gtacattatc aagtggatgt gatggtgccc     60
ctctgcttcc tctgctgttt attattgtaa acataggttt caatattgca ttgcttcatc    120
tcctcaagat ctcttcagct gttgtatctt gtcttgcttc cacattttca gtcccaatat    180
ccatctacgt gttcaccatg ccattgccat accttggtgt tgcctcctct cttccaacag    240
gctttatggc aggggccatt atcctcattt gggcttact  catttatgct ggaccccctt    300
caaatggttc ctcgggtgct tccttctcaa cttcctccac ctagagaggc tagaatgagt    360
tgacatgtca ttgcagatag tacaacacca caaggaacta attcaggttc gcttttagga    420
gacggctata agaaggagaa agaaataggg cgttcttgta agttgtaata gttgttcgta    480
agcatttttt atgagctaag cttaagtaag aaagagacta gactatagat agaacaggtt    540
ccaagttcaa tttttatgta agctaaggaa agtaaataga gaataaaagt cactttgttg    600
acagaggaaa tgatattgga ccatttggat gcaaaaaaaa aaaaaaa                  647
```

<210> SEQ ID NO 3
<211> LENGTH: 113
<212> TYPE: PRT
<213> ORGANISM: Glycine max

<400> SEQUENCE: 3

```
Asp Gly Ala Ala Cys Phe Leu Asn Phe Gly Thr Leu Ser Ser Gly Cys
1               5                   10                  15

Asp Gly Ala Pro Leu Leu Pro Leu Leu Phe Ile Ile Val Asn Ile Gly
            20                  25                  30

Phe Asn Ile Ala Leu Leu His Leu Leu Lys Ile Ser Ser Ala Val Val
        35                  40                  45

Ser Cys Leu Ala Ser Thr Phe Ser Val Pro Ile Ser Ile Tyr Val Phe
    50                  55                  60

Thr Met Pro Leu Pro Tyr Leu Gly Val Ala Ser Ser Leu Pro Thr Gly
65                  70                  75                  80

Phe Met Ala Gly Ala Ile Ile Leu Ile Leu Gly Leu Leu Ile Tyr Ala
                85                  90                  95

Trp Thr Pro Ser Asn Gly Ser Ser Gly Ala Ser Phe Ser Thr Ser Ser
            100                 105                 110

Thr
```

<210> SEQ ID NO 4
<211> LENGTH: 276
<212> TYPE: PRT
<213> ORGANISM: Arabidopsis thaliana

<400> SEQUENCE: 4

```
Met Leu Ser Val Pro Lys Ser Pro Phe Leu Ile Val Gly Ile Leu Glu
1               5                   10                  15

Ala Leu Ala Ala Ala Gly Met Ala Ala Ala Ala Asn Leu Ser Gly
            20                  25                  30

Pro Ser Thr Thr Val Leu Ser Gln Arg Lys Pro Asn Thr Arg Met Tyr
```

```
                35                  40                  45
Ser Cys Ser Ser Arg Cys Asn Arg Gln Cys Gly Lys Val Arg Ser Ala
 50                  55                  60

Phe Val Leu Ile Phe Cys Gly Ser Gly Ala Ala His Ser Leu Asn Glu
 65                  70                  75                  80

Ala Gly Val Leu Trp Ile Leu Met Val Leu Ser Phe Leu Leu Gln
                 85                  90                  95

Gly Ala Gly Thr Val Leu Lys Glu Val Ile Phe Ile Asp Ser Gln Arg
                100                 105                 110

Arg Leu Lys Gly Ala Ser Leu Asp Leu Phe Ile Val Asn Ser Tyr Gly
                115                 120                 125

Ser Ala Phe Gln Ala Ile Cys Ile Ala Leu Leu Pro Phe Leu Ser
                130                 135                 140

Lys Leu Trp Gly Ile Pro Phe Asn Gln Leu Gly Thr Tyr Leu Lys Asp
145                 150                 155                 160

Gly Ala Val Cys Phe Leu Asn Asn Gly Thr Ile Thr Lys Gly Cys Asp
                165                 170                 175

Gly Ala Pro Phe Leu Pro Leu Leu Phe Val Ile Met Asn Ile Gly Tyr
                180                 185                 190

Asn Ile Ala Leu Leu Arg Leu Leu Lys Ile Ser Ser Ala Val Val Ser
                195                 200                 205

Cys Leu Ala Ser Thr Val Ser Val Pro Ile Ala Val Phe Leu Phe Thr
210                 215                 220

Met Pro Leu Pro Tyr Leu Gly Val Ala Ser Ser Leu Pro Lys Gly Phe
225                 230                 235                 240

Met Gly Gly Thr Ile Ile Leu Val Leu Gly Met Ile Leu Tyr Ser Trp
                245                 250                 255

Thr Pro His Gly Ala Asn Ser Ser His Thr Asp Ser Val Ile Pro Ser
                260                 265                 270

Pro Pro Pro Thr
                275

<210> SEQ ID NO 5
<211> LENGTH: 25
<212> TYPE: DNA
<213> ORGANISM: Artificial
<220> FEATURE:
<223> OTHER INFORMATION: primer sequence

<400> SEQUENCE: 5
cccggggctc gcgttagttc cactc                                        25

<210> SEQ ID NO 6
<211> LENGTH: 28
<212> TYPE: DNA
<213> ORGANISM: Artificial
<220> FEATURE:
<223> OTHER INFORMATION: primer sequence

<400> SEQUENCE: 6
ggcgcgcctg catctgtgac agttccag                                     28

<210> SEQ ID NO 7
<211> LENGTH: 28
<212> TYPE: DNA
<213> ORGANISM: Artificial
<220> FEATURE:
<223> OTHER INFORMATION: primer sequence

<400> SEQUENCE: 7
```

-continued

```
acgtctgcag cgggtcagag ttggcttc                                          28

<210> SEQ ID NO 8
<211> LENGTH: 29
<212> TYPE: DNA
<213> ORGANISM: Artificial
<220> FEATURE:
<223> OTHER INFORMATION: primer sequence

<400> SEQUENCE: 8
agctctgcag gctaactttg tgagggttg                                         29

<210> SEQ ID NO 9
<211> LENGTH: 22
<212> TYPE: DNA
<213> ORGANISM: Artificial
<220> FEATURE:
<223> OTHER INFORMATION: primer sequence

<400> SEQUENCE: 9
tgcaggcgcg cctgcatctg tg                                                22
```